(12) United States Patent
Mathews et al.

(10) Patent No.: US 12,315,634 B1
(45) Date of Patent: May 27, 2025

(54) AUTONOMOUS MIRRORING DIAGNOSTIC, NAVIGATION, AND ADVICE SYSTEM AND A MIRRORED INTELLIGENCE METHOD

(71) Applicants: Michael Lee Mathews, Broken Arrow, OK (US); Pamela M Mathews, Broken Arrow, OK (US); Tiffany Lee Mathews, Broken Arrow, OK (US); Jessica Lynn Angsomwine, Cypress, TX (US)

(72) Inventors: Michael Lee Mathews, Broken Arrow, OK (US); Pamela M Mathews, Broken Arrow, OK (US); Tiffany Lee Mathews, Broken Arrow, OK (US); Jessica Lynn Angsomwine, Cypress, TX (US)

( * ) Notice: Subject to any disclaimer, the term of this patent is extended or adjusted under 35 U.S.C. 154(b) by 512 days.

(21) Appl. No.: 17/869,783

(22) Filed: Jul. 20, 2022

Related U.S. Application Data (60) Provisional application No. 63/223,858, filed on Jul. 20, 2021.

(51) Int. Cl.
*G16H 50/20* (2018.01)
*G06F 3/01* (2006.01)
*G06F 3/04847* (2022.01)

(52) U.S. Cl.
CPC ............ *G16H 50/20* (2018.01); *G06F 3/011* (2013.01); *G06F 3/04847* (2013.01)

(58) Field of Classification Search
CPC ...... G16H 50/20; G06F 3/011; G06F 3/04847
See application file for complete search history.

(56) References Cited

U.S. PATENT DOCUMENTS

| | | | |
|---|---|---|---|
| 10,052,026 B1 * | 8/2018 | Tran | A61B 5/165 |
| 2017/0199576 A1 * | 7/2017 | Schmitz-Le Hanne | G06F 1/1605 |
| 2017/0319148 A1 * | 11/2017 | Shahin | A61B 5/0079 |
| 2018/0373330 A1 * | 12/2018 | Benford | G06V 10/25 |
| 2019/0272675 A1 * | 9/2019 | Wagner | H04N 23/57 |
| 2019/0339936 A1 * | 11/2019 | Brahimi | G10L 15/22 |
| 2023/0071274 A1 * | 3/2023 | Trehan | G06T 13/40 |

* cited by examiner

*Primary Examiner* — William L Bashore
*Assistant Examiner* — Gregory A Distefano
(74) *Attorney, Agent, or Firm* — Plager Schack LLP; Mark H. Plager, Esq.; Stephen Hallberg, Esq.

(57) ABSTRACT

An autonomous mirroring diagnostic, navigation, and advice system and a mirrored intelligence method for engaging individuals to mirror personalized information normally accessible in a clinical setting in an engaged and autonomous manner to allow for self-diagnosis, navigation, and advice across any personalized AI device are disclosed. By seamlessly integrating normally accessible processes in a clinical setting the autonomous mirroring diagnostic, navigation, and advice system and mirrored intelligence method allow for self-diagnostic, navigation, and advice via a mirror or device.

6 Claims, 5 Drawing Sheets

FIG. 5 ed the Jul. 20, 2021. The U.S.
AUTONOMOUS MIRRORING DIAGNOSTIC, NAVIGATION, AND ADVICE SYSTEM AND A MIRRORED INTELLIGENCE METHOD

CLAIM OF BENEFIT TO PRIOR APPLICATION

This application claims benefit to U.S. Provisional Patent Application 63/223,858, entitled "Method to engage individuals to mirror personalized information in an engaged and autonomous manner," filed Jul. 20, 2021. The U.S. Provisional Patent Application 63/223,858 is incorporated herein by reference.

BACKGROUND

Embodiments of the invention described in this specification relate generally to advice, self-reflection, and guidance technology, and more particularly, to an autonomous mirroring diagnostic, navigation, and advice system and a mirrored intelligence method for engaging individuals to mirror personalized information normally accessible in a clinical setting in an engaged and autonomous manner to allow for self-diagnosis, navigation, and advice across any personalized AI device.

With all the digital information in the world people struggle by not having an automated visual and audio method to nudge them with the right information at the right time. People are overwhelmed by the amounts of data.

The former devices and systems focus on a niche such as fitness, education, calendars, online banking. They force the user to spend hours searching and using the smartphone that distracts from the real issues of the day. The devices in essence make us servants to the technology or device, rather than using the technology to advise, nudge, and automate the immediate and most important elements.

Therefore, what is needed is a way to seamlessly integrate normally accessible processes that are typically only available through a clinical setting in any environment, setting, sphere, or location in a way that enables a person to feel secure and allows for self-diagnostic, navigation, and advice across any personalize AI device.

BRIEF DESCRIPTION

A novel autonomous mirroring diagnostic, navigation, and advice system and a novel mirrored intelligence method for engaging individuals to mirror personalized information normally accessible in a clinical setting in an engaged and autonomous manner to allow for self-diagnosis, navigation, and advice across any personalized AI device are disclosed. In some embodiments, the autonomous mirroring diagnostic, navigation, and advice system includes a software-implemented mirrored intelligence (MQ) application for engaging individuals to mirror personalized information which is normally only accessible in a clinical setting. In this way, the mirrored intelligence (MQ) application engages individuals to mirror personalized information in a way that allows for self-diagnosis, navigation, and advice across any personalized AI device to improve the well-being of such individuals.

In some embodiments, the autonomous mirroring diagnostic, navigation, and advice system is configured to operate by a mirrored intelligence (MQ)-blended operating system in connection with a plurality of primary open source components and a plurality of propriety system components and by way of the MQ application.

In some embodiments, the autonomous mirroring diagnostic, navigation, and advice system comprises an enhanced autonomous mirroring diagnostic, navigation, and advice system that is configured to operate by way of the MQ-blended operating system in connection with a plurality of enhanced open source components (which includes the plurality of primary open source components) and the plurality of propriety system components and by way of the MQ application.

In some embodiments, the autonomous mirroring diagnostic, navigation, and advice system is configured to operate as a cloud-based software-as-a-service ("SaaS") autonomous mirroring diagnostic, navigation, and advice system. In some embodiments, the cloud-based SaaS autonomous mirroring diagnostic, navigation, and advice system hosts a cloud application service to which any type of personalized AI device connects when running the MQ application in order to engage individuals to mirror personalized information to allow for self-diagnosis, navigation, and to provide advice or nudging suggestions.

In some embodiments, the mirrored intelligence method for engaging individuals to mirror personalized information normally accessible in a clinical setting in an engaged and autonomous manner to allow for self-diagnosis, navigation, and advice across any personalized AI device comprises a plurality of steps. The plurality of steps in some embodiments of the mirrored intelligence method comprise (i) filling out a skills template that allows the individual user to decide which nudging elements will be configured for use and which actions of the nudging elements should be specified to encourage one or another option to the user, where the nudging elements correspond to various hardware and software modules that are communicably connected to a mirrored intelligence (MQ) blended operating system and associated nudging database, (ii) selecting, by the user, display, audible, textual, or other formats to configure for each of the nudging elements via the skills template, (iii) translating the actions of the nudging elements and selected displays corresponding to the nudging elements to utilize the system in the appropriate languages and with the appropriate utilities, (iv) manufacturing or outsourcing personalized AI devices for users (manufacturing only as needed) or provisioning existing personalized AI devices needed by users to access and interact with the MQ-blended operating system running on the device and the nudging database in association with the system, (v) programming, by the user, the nudging sequence with the appropriate software and utilities (via a mirrored intelligence (MQ) application) to ensure that user preferences can be accessed, timed, and opened through related software applications for the corresponding personalized AI device, (vi) providing the autonomous voice, text, and video that will be output for the desired nudging outcomes, (vii) configuring the nudging data to accommodate the services utilized by the user, whether on a paid subscription model or unpaid service free model, and optionally, (viii) adding one or more open source applications to the services and combined personalized AI devices and mirrored intelligence (MQ) application and nudging settings and configuration parameters as set by the user, such as two-way video conferencing, web conferencing (via web camera), security, facial recognition, biomedical applications, etc., which are accessed and utilized beyond core modules for the nudging elements and corresponding nudging actions.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein:

FIG. 5 conceptually illustrates

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide an autonomous mirroring diagnostic, navigation, and advice system and a mirrored intelligence method for engaging individuals to mirror personalized information normally accessible in a clinical setting in an engaged and autonomous manner to allow for self-diagnosis, navigation, and advice across any personalized AI device. In some embodiments, the autonomous mirroring diagnostic, navigation, and advice system includes a software-implemented mirrored intelligence (MQ) application for engaging individuals to mirror personalized information which is normally only accessible in a clinical setting. In this way, the mirrored intelligence (MQ) application engages individuals to mirror personalized information in a way that allows for self-diagnosis, navigation, and advice across any personalized AI device to improve the well-being of such individuals.

In some embodiments, the autonomous mirroring diagnostic, navigation, and advice system is configured to operate by a mirrored intelligence (MQ)-blended operating system in connection with a plurality of primary open source components and a plurality of propriety system components and by way of the MQ application.

In some embodiments, the autonomous mirroring diagnostic, navigation, and advice system comprises an enhanced autonomous mirroring diagnostic, navigation, and advice system that is configured to operate by way of the MQ-blended operating system in connection with a plurality of enhanced open source components (which includes the plurality of primary open source components) and the plurality of propriety system components and by way of the MQ application.

In some embodiments, the autonomous mirroring diagnostic, navigation, and advice system is configured to operate as a cloud-based software-as-a-service ("SaaS") autonomous mirroring diagnostic, navigation, and advice system. In some embodiments, the cloud-based SaaS autonomous mirroring diagnostic, navigation, and advice system hosts a cloud application service to which any type of personalized AI device connects when running the MQ application in order to engage individuals to mirror personalized information to allow for self-diagnosis, navigation, and to provide advice or nudging suggestions.

In some embodiments, the mirrored intelligence method for engaging individuals to mirror personalized information normally accessible in a clinical setting in an engaged and autonomous manner to allow for self-diagnosis, navigation, and advice across any personalized AI device comprises a plurality of steps. The plurality of steps in some embodiments of the mirrored intelligence method comprise (i) filling out a skills template that allows the individual user to decide which nudging elements will be configured for use and which actions of the nudging elements should be specified to encourage one or another option to the user, where the nudging elements correspond to various hardware and software modules that are communicably connected to a mirrored intelligence (MQ) blended operating system and associated nudging database, (ii) selecting, by the user, display, audible, textual, or other formats to configure for each of the nudging elements via the skills template, (iii) translating the actions of the nudging elements and selected displays corresponding to the nudging elements to utilize the system in the appropriate languages and with the appropriate utilities, (iv) manufacturing or outsourcing personalized AI devices for users (manufacturing only as needed) or provisioning existing personalized AI devices needed by users to access and interact with the MQ-blended operating system running on the device and the nudging database in association with the system, (v) programming, by the user, the nudging sequence with the appropriate software and utilities (via a mirrored intelligence (MQ) application) to ensure that user preferences can be accessed, timed, and opened through related software applications for the corresponding personalized AI device, (vi) providing the autonomous voice, text, and video that will be output for the desired nudging outcomes, (vii) configuring the nudging data to accommodate the services utilized by the user, whether on a paid subscription model or unpaid service free model, and optionally, (viii) adding one or more open source applications to the services and combined personalized AI devices and mirrored intelligence (MQ) application and nudging settings and configuration parameters as set by the user, such as two-way video conferencing, web conferencing (via web camera), security, facial recognition, biomedical applications, etc., which are accessed and utilized beyond core modules for the nudging elements and corresponding nudging actions.

As stated above, with all the digital information in the world people struggle by not having an automated visual and audio method to nudge them with the right information at the right time. People are overwhelmed by the amounts of data. The former devices and systems focus on a niche such as fitness, education, calendars, online banking. They force the user to spend hours searching and using the smartphone that distracts from the real issues of the day. The devices in essence make us servants to the technology or device, rather than using the technology to advise, nudge, and automate the immediate and most important elements. Embodiments of the autonomous mirroring diagnostic, navigation, and advice system and the mirrored intelligence method described in this specification solve such problems by a Mirrored Intelligence ("MQ") software implementation. Specifically, the Mirrored Intelligence (MQ) software application expands and personalizes the usefulness of all digital data to improve the well-being of people. It is available via any smart mirror, smart TV, smart glasses, and any other slim-digital device. However, the Mirrored Intelligence (MQ) application of the autonomous mirroring diagnostic, navigation, and advice system does not require a smart phone or a computer. The Mirrored Intelligence (MQ) application integrates the best of all technology in a micro-fashion. This includes using open and specialized programming language such as magic-mirror coding, NLP language, etc. In essence, it reverses the focus on tech 1.0, 2.0, 3.0 and helps acclimate people to the digital world so we can say digital life 1.0, 2.0. 3.0.

Embodiments of the autonomous mirroring diagnostic, navigation, and advice system and the mirrored intelligence method described in this specification differ from and improve upon currently existing options. In particular, the autonomous mirroring diagnostic, navigation, and advice system and the mirrored intelligence method, implemented by the Mirrored Intelligence (MQ) application, is the first utility that focuses the integration of converged technology and media to help individuals in every aspect of life. As such, the autonomous mirroring diagnostic, navigation, and advice system and the mirrored intelligence method of the present disclosure provide the first comprehensive personal well-being utility available across all platforms.

The past and existing systems, devices, and methods focus on particular niche areas or aspects of any individual's life, such as fitness, education, calendaring/scheduling, online banking, etc. These existing options force the user to spend hours searching and using their smartphone, mobile device, or other device in ways that are almost constant and which district them from the real issues of the day. The existing options seem to have an effect that is different from the intention—that is, the existing systems, devices, and methods in essence make us servants to technology, rather than beneficial assistive devices/systems which leverage the technology to advise, nudge, and automate the immediate and most important aspects or elements in life.

While historically it has been cost prohibitive to design a method to self-diagnose life circumstances, the autonomous mirroring diagnostic, navigation, and advice system and the mirrored intelligence method of the present disclosure seamlessly integrates processes and aspects that are normally only accessible through the clinical setting, thereby providing an effective solution for self-diagnostic, navigation, and advice across any personalized AI device.

The autonomous mirroring diagnostic, navigation, and advice system and the mirrored intelligence method of the present disclosure may be comprised of the following elements. This list of possible constituent elements is intended to be exemplary only and it is not intended that this list be used to limit the autonomous mirroring diagnostic, navigation, and advice system and the mirrored intelligence method of the present application to just these elements. Persons having ordinary skill in the art relevant to the present disclosure may understand there to be equivalent elements that may be substituted within the present disclosure without changing the essential function or operation of the autonomous mirroring diagnostic, navigation, and advice system and the mirrored intelligence method.

1. Complete a skills template that allows an individual to decide what nudging elements are being requested.
2. Allow user to select the various formats they want their nudging via the skills template to be displayed on. This could include all, one, two, three. The purpose is to ensure they purchase the right device and all audio, text and video can be displayed and supplied.
3. Translate the nudging actions and selected displays to utilize the appropriate languages and utilities.
4. Manufacture or outsource the devices user purchases (if needed), In many cases users will already have some of the devices and only need access to login into the nudging database.
5. Program the nudging sequence with the appropriate software and utilities to ensure user preferences can be accesses, times, and open the related software apps.
6. Provide the autonomous voice, text, and video that will be displayed for the desired nudge outcomes.
7. Configure the nudging database to accommodate the user subscription services
8. Add any open source applications to the purchased and combined devices and nudging application such as two-way video, web conferencing, security, facial recognition, biomedical. These will all be repurchased commercial apps or open source.

The autonomous mirroring diagnostic, navigation, and advice system and the mirrored intelligence method of the present disclosure generally works by carrying out the steps above. Each component and/or device leverages the modern methodologies of connecting Internet-of-Things protocols, web-based coding, TV-based programming with Amazon Skills, etc. The integration of each of these known and proven methodologies is finally converted and translated into the proper format of display including NLP, Magic-Mirror Coding, and PHP scripting language.

The meta layer logic gates are dependent on each device or application chosen. The meta layer logic leverages open APIs to ensure all data is passed between utilities and applications. The micro layer logic is done with Amazon skills programming and magic-mirror programming, and Natural language programming.

To make the autonomous mirroring diagnostic, navigation, and advice system and the mirrored intelligence method of the present disclosure, an individual may assemble components and products and integrate/implement software. This may include a large number of commercially-available products, software, or other technology. The products and components would be configured in ways to help individuals. Thus, one would personalize the products to help individuals, integrate the commercialized products, automate the products and services to focus on people's needs to be nudged into the correct actions, and provide as much autonomous activity across the devices and services to make everything seamless. Approximately five percent (~5%) of specialized integration and automation is what has proven to be lacking. However, very few skills, talents, and knowledge exist to make the automation, autonomous activity, and subscription services possible to sell as a service.

To use the autonomous mirroring diagnostic, navigation, and advice system and the mirrored intelligence method of the present disclosure, a person would use the Mirrored Intelligence (MQ) application to better focus on themselves rather than the technology itself. A person can now use a TV, Mirror, Facebook Portal, BOSE AI Glasses, Amazon Firestick to get insights and, reflections of their current status in every area of life. As an example, a person can use any of the devices above and take the national depression test. They can see, hear, or display their depression results without anyone else seeing. This same concept works for all personal records such as an educational transcript, an online course, a banking statement, IRS taxes. The Amazon Skills makes this all programmable and possible. It in essence this invention personalizes all internet, AI, data science, and machine learning. Just as Internet of Things (IoT) makes the Internet reachable by things/devices, this invention allows the Internet to become the Internet-of-nudging people with personalized and actionable information.

Figure 1:
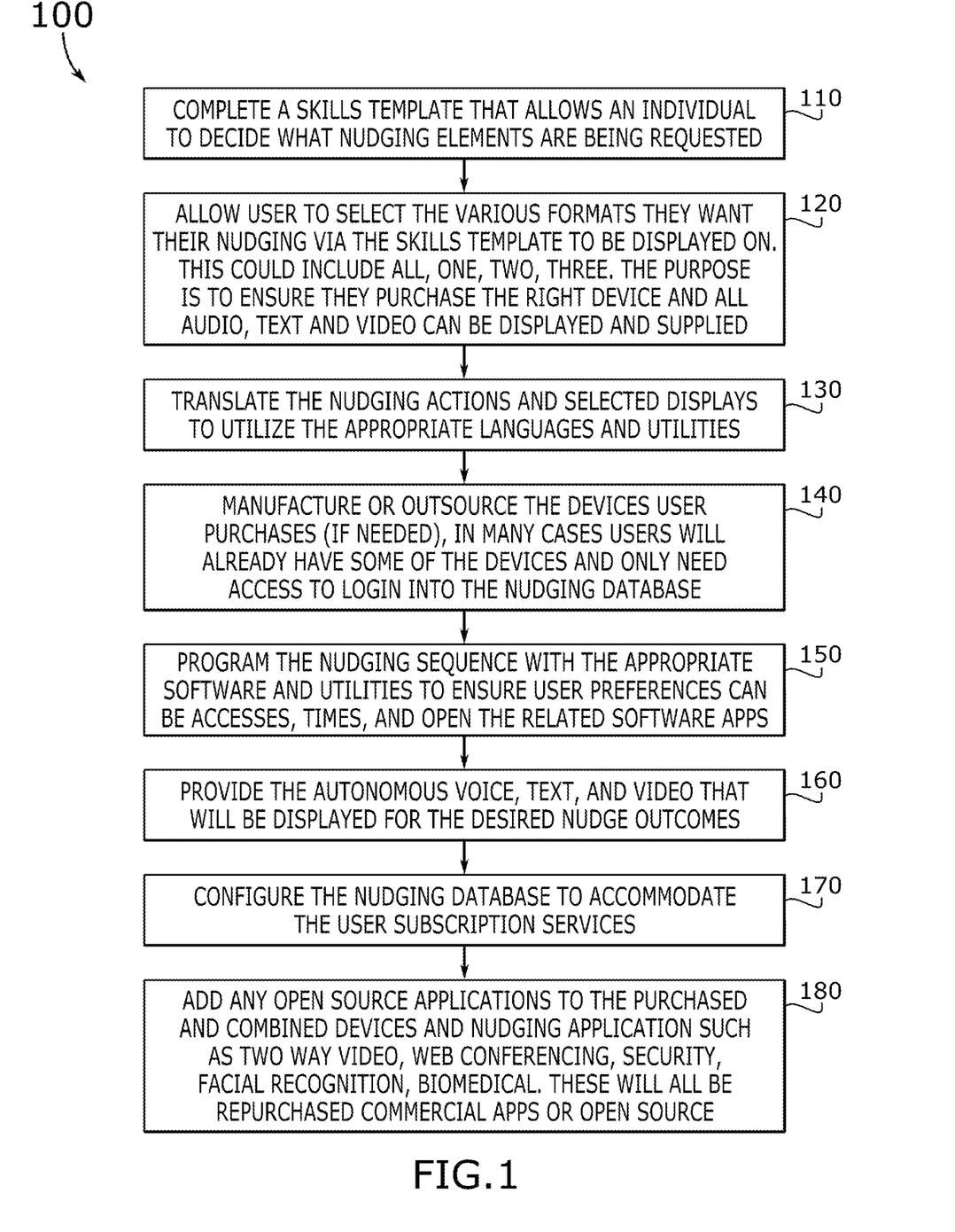
FIG. 1 conceptually illustrates a mirrored intelligence method in some embodiments for engaging individuals to mirror personalized information normally accessible in a clinical setting in an engaged and autonomous manner to allow for self-diagnosis, navigation, and advice across any personalized AI device.

By way of example, FIG. 1 conceptually illustrates a mirrored intelligence method 100 for engaging individuals to mirror personalized information normally accessible in a clinical setting in an engaged and autonomous manner to allow for self-diagnosis, navigation, and advice across any personalized AI device. In some embodiments, the mirrored intelligence method 100 is performed by a user interacting with the mirrored intelligence (MQ) application.

In some embodiments, the mirrored intelligence method 100 starts by filling out a skills template (at 110). The skills template allows the individual user to decide which nudging elements will be configured for use. The nudging elements include actions that encourage one or another option to the user. The nudging elements correspond to various hardware and software modules that are communicably connected to a mirrored intelligence (MQ) blended operating system and associated nudging database in various embodiments of the autonomous mirroring diagnostic, navigation, and advice system. Examples of different embodiments of the autonomous mirroring diagnostic, navigation, and advice system are described further below, by reference to FIGS. 2-4. By selecting the nudging elements in the skills template, the user is making selections for nudging elements to be requested and loaded for use at runtime, and otherwise made available when the user starts interaction and the system is put to use.

In some embodiments, the mirrored intelligence method 100 continues to a next step for the user to select the formats for the nudging elements (at 120), as selected by the user via the skills template. The various formats are those formats on which the user would like for the nudging elements to be displayed. The user can select one, two, three, or all of the various formats. The purpose is to ensure that the user configures the setting for the nudging elements for the right device. For instance, a smart mirror or a smart TV may be the user's device. The selection of formats ensures that audio, textual, and visual (video) can be output according to the format native to the corresponding device (which in some cases may support multiple formats (e.g., video+audio+text).

In some embodiments, the mirrored intelligence method 100 proceeds to the next step for translating the actions of the nudging elements and selected displays corresponding to the nudging elements (at 130) to utilize the system in the appropriate languages and with the appropriate utilities.

In some embodiments, the mirrored intelligence method 100 includes another step for manufacturing or outsourcing the devices the user purchases (at 140). The step for manufacturing or outsourcing the devices the user purchases (at 140) is performed by the mirrored intelligence method 100 only when needed. Therefore, this step for manufacturing or outsourcing the devices the user purchases (at 140) may be optional in some embodiments. For instance, in many cases, users will already have some of the devices and would only need to access those devices to login to access the nudging database in association with the system.

In some embodiments, the mirrored intelligence method 100 proceeds forward to a step at which the user programs the nudging sequence (at 150) with the appropriate software and utilities to ensure that user preferences can be accessed, timed, and opened through related software applications. For instance, the user may interact with a configuration or settings screen of the mirrored intelligence (MQ) application to program the nudging sequence.

In some embodiments, the mirrored intelligence method 100 then continues forward to a step for providing the autonomous voice, text, and video (at 160) that will be output for the desired nudging outcomes. For example, text and video are displayed, autonomous voice is audibly outcome, an audio portion of the video is also audibly output while the video portion is displayed.

Next, the mirrored intelligence method 100 of some embodiments configures the nudging data (at 170) to accommodate the services utilized by the user. For instance, the user may subscribe to multiple services on a paid service-level subscription agreement, or in some cases there may be free service levels with options to pay for further/additional subscription services.

In some embodiments, the mirrored intelligence method 100 includes an optional step for adding one or more open source applications to the purchased services and combined devices and mirrored intelligence (MQ) application and nudging parameters as set by the user (at 180). This optional step is completed when optional additions, such as two-way video conferencing, web conferencing (via web camera), security, facial recognition, biomedical, etc., are utilized beyond the core configured modules for the nudging elements and corresponding nudging actions.

Figure 2:
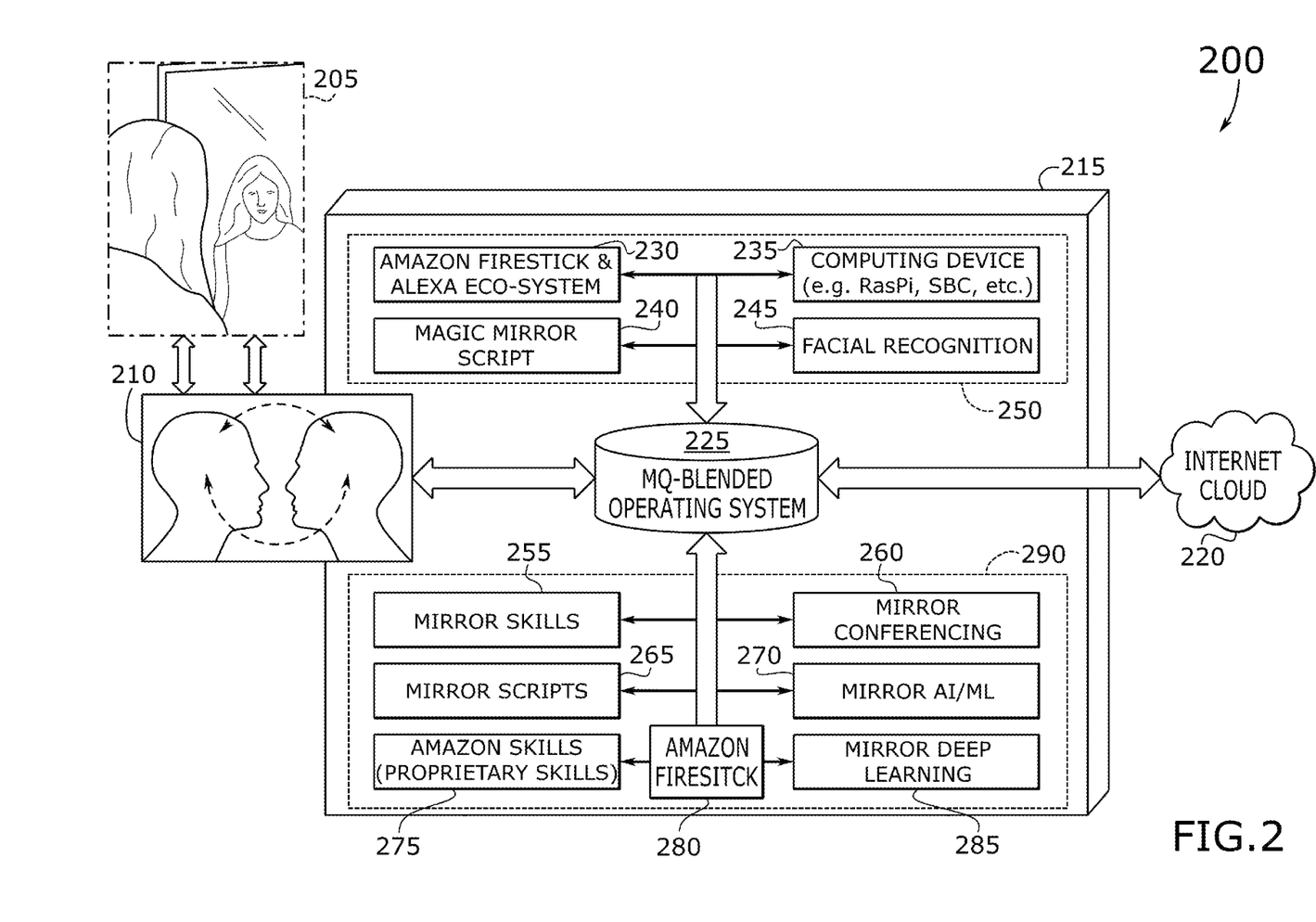
FIG. 2 conceptually illustrates an autonomous mirroring diagnostic, navigation, and advice system in some embodiments.

By way of example, FIG. 2 conceptually illustrates an autonomous mirroring diagnostic, navigation, and advice system 200 in some embodiments. As shown in this figure, the autonomous mirroring diagnostic, navigation, and advice system 200 shows a user self-reflection 205 for interaction 210 with a smart mirror 215. The smart mirror 215 itself includes a mirrored intelligence (MQ)-blended operating system 225 that is configured for network communication to/from the internet 220 (or referred to as "internet cloud 220"). The smart mirror 215 also includes a plurality of open source-based modules/components 250 (hereinafter referred to collectively as the "plurality of open source-based modules 250" or the "open source-based modules 250") a plurality of proprietary mirror components/modules 290 (hereinafter referred to collectively as the "plurality of proprietary mirror modules 290" or the "proprietary mirror modules 290"). The plurality of open source-based modules 250 and the plurality of proprietary mirror modules 290 are communicably connected to the MQ-blended operating system 225 and are accessed by the MQ-blended operating system 225 as needed based on the interaction 210 of user (via user self-reflection 205) with video, textual, or audio output from the smart mirror 215. In some embodiments, data and configuration settings for all of the open source-based modules 250 and the proprietary mirror modules 290 are stored in the nudging database associated with the MQ-blended operating system 225.

In particular, the plurality of open source-based modules 250 for the autonomous mirroring diagnostic, navigation, and advice system 200 comprises an Amazon firestick and Alexa eco-system module 230, a computing device 235, a magic mirror script 240, and a facial recognition module 250. The computing device 235 can be any type of single board computer ("SBC"), such as a Raspberry Pi or other SBC. The magic mirror script 240 can be written in a magic mirror scripting language or other scripting language with APIs and libraries to support magic mirror functioning. Note that the device of choice may be different from the smart mirror 215 shown in this figure—for instance, a smart TV or other smart device—in which case the script is based on the functions and features of the smart device. The facial recognition module 245 is configured to identified the face of the user when the user is in view of the smart mirror 215. In some embodiments, the facial recognition module 245 uses a deep learning system to refine its ability to accurately identify faces over time. Also, although the plurality of open source-based modules 250 for the autonomous mirroring diagnostic, navigation, and advice system 200 shown in this figure is the Amazon firestick and Alexa eco-system module 230, the autonomous mirroring diagnostic, navigation, and advice system 200 is configured to support any other comparable commercial device and voice-assistance smart hub eco-system.

Similarly, the plurality of proprietary mirror modules 290 comprises mirror skills 255, a mirror conferencing module 260, mirror scripts 265, a mirror artificial intelligence (AI)/machine learning (ML) module 270, an Amazon skills module 275, an Amazon firestick device 280 and a mirror deep learning module 285. In particular, data and configuration settings each of the proprietary mirror modules 290 are stored in the nudging database associated with the MQ-blended operating system 225. In some embodiments, the mirror skills 255 and mirror scripts 265 are stored in the nudging database associated with the MQ-blended operating system 225. The mirror skills 255 and the mirror scripts 265 may include skills and scripts developed by a manufacturer of the smart mirror 215 and/or the user. In some embodiments, the mirror AI/ML module 270 and the mirror deep learning module 285 are communicably connected to the computing device 235 and configured to run locally within the smart mirror 215. However, in some embodiments, either or both of the mirror AI/ML module 270 and the mirror deep learning module 285 run partially by connection to external, Internet services. Specifically, in some embodiments, the MQ-blended operating system 225 accesses the internet cloud 220 to access external services (such as deep learning processing, AI/ML processing, etc.) and/or to tap a plurality of configuration settings and data stored in a service provider host, such as Amazon web services. In some embodiments, the Amazon firestick device 280 facilitates the interaction between the MQ-blended operating system 225 and the Amazon host cloud services. Thus, the Amazon skills module 275 may reference proprietary skills created by the user or by a manufacturer of the smart mirror 215 which are stored (at least in part) within the Amazon web services accessed over the internet cloud 220. The mirror conferencing module 260 similarly accesses conferencing communication over the internet cloud 220.

Figure 3:
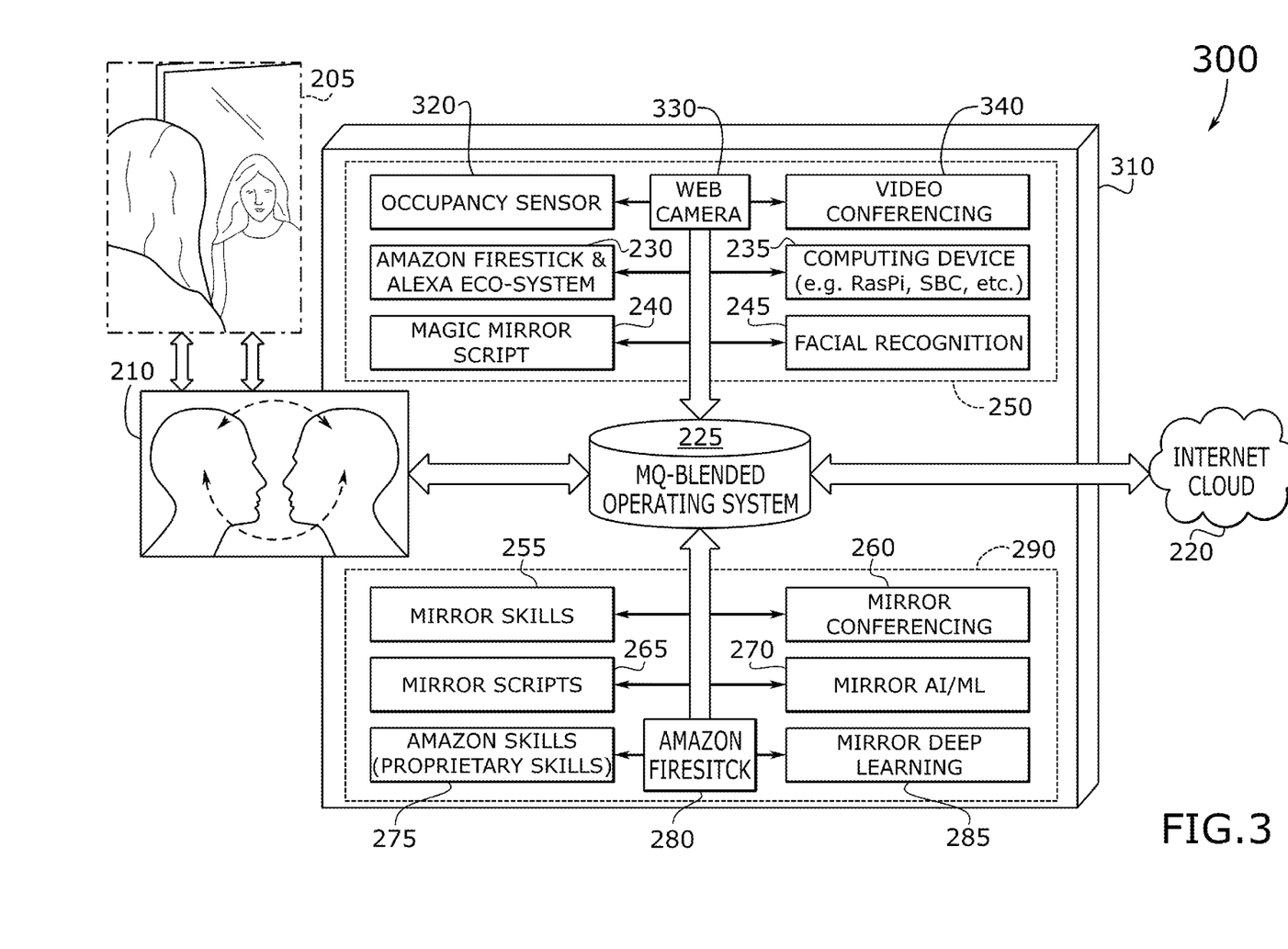
FIG. 3 conceptually illustrates an enhanced autonomous mirroring diagnostic, navigation, and advice system in some embodiments.

Turning to another example, FIG. 3 conceptually illustrates an enhanced autonomous mirroring diagnostic, navigation, and advice system 300 in some embodiments. As shown in this figure, the enhanced autonomous mirroring diagnostic, navigation, and advice system 300 includes the user self-reflection 205 for interaction 210 with an enhanced smart mirror 310. The enhanced smart mirror 310 itself includes the mirrored intelligence (MQ)-blended operating system 225, which communicates over the internet cloud 220 to various services and/or to access various data or settings. The enhanced smart mirror 310 also includes the plurality of proprietary mirror modules 290 and plurality of open source-based modules/components 250. While the plurality of proprietary mirror modules 290 are the same as those described above, by reference to FIG. 2, the plurality of open source-based modules/components 250 includes additional modules/components not present in the autonomous mirroring diagnostic, navigation, and advice system 200 described above, by reference to FIG. 2. Specifically, the plurality of open source-based modules/components 250 for the smart mirror 310 of the autonomous mirroring diagnostic, navigation, and advice system 300 includes an occupancy sensor 320, a web camera 330, and a video conferencing module 340.

In some embodiments, the occupancy sensor 320 is configured to detect motion, detect and recognize facial expressions, and perform facial expression comparisons with a plurality of previous facial expressions captured in images of a particular user or a period of time. The images would be captured by the web camera 330. For example, the occupancy sensor 320 may detect a facial expression of a user and compare to images captured by the web camera 330 of the user's typical facial expression for the past ten days—and if a noticeable difference in expression is detected, the occupancy sensor 320 of some embodiments triggers a script to offer a suggestion or otherwise interact with the user (e.g., "Hi there, I notice that you look down today. Would you like to connect with someone?"). If the user interacts in response in the affirmative (e.g., "Yes, I'd like to connect with someone."), then the video conferencing module 340 is triggered to start a video conference to connect the user with someone. In some embodiments, the facial expression comparison is based on machine learning and AI performed by the mirror AI/ML module 270 and the mirror deep learning module 285. The more images of facial expressions captured by the smart mirror 310, the more samples available for the mirror deep learning module 285 to accurately detect and recognize different facial expressions.

Also, the difference between the occupancy sensor 320 and the facial recognition module 245 is that the occupancy sensor 320 operates when the identity of the user in front of the mirror (or other smart device) is known. The identity of the user is, of course, ascertained by the facial recognition module 245. Thus, the occupancy sensor 320 works in connection with the facial recognition module 245 since detecting changes in facial expressions on a routine basis is largely dependent on the identity of the individual user who is presented in front of the mirror.

In some embodiments, the autonomous mirroring diagnostic, navigation, and advice system operates in part by network connection to a cloud application service and one or more external (e.g., third party) services. In some embodiments, logic processing of the MQ-blended operating system is performed in part by a software application web service (or a software-as-a-service "SaaS") hosted by a cloud-based server to which individual personalized AI user devices running the mirrored intelligence (MQ) application connect over the cloud (or Internet). An example of such a SaaS cloud application service is described next, by reference to FIG. 4.

Figure 4:
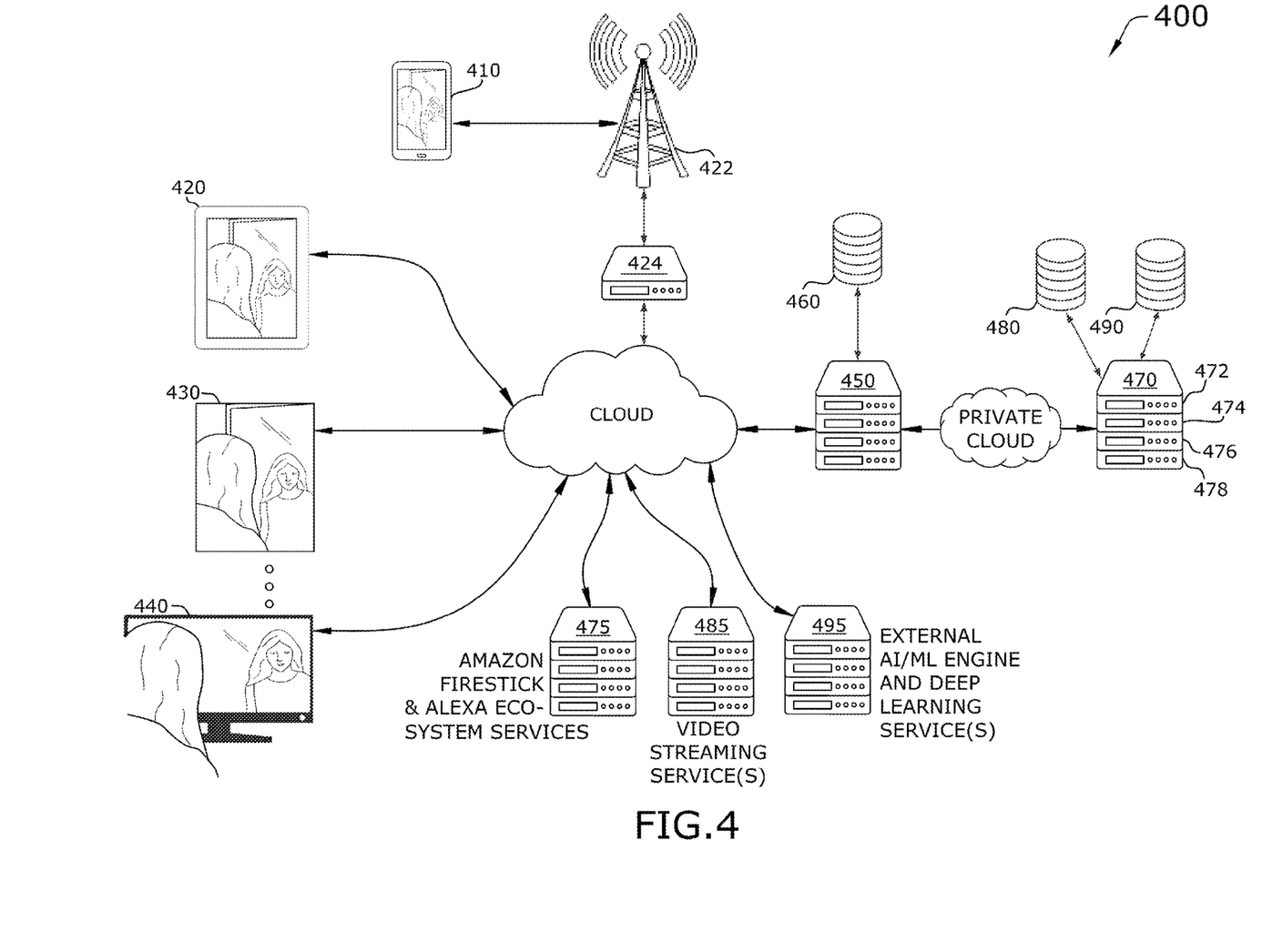
FIG. 4 conceptually illustrates a network architecture of a cloud-based autonomous mirroring diagnostic, navigation, and advice system in some embodiments that hosts a cloud application service to which any personalized AI device connects to engage individuals to mirror personalized information normally accessible in a clinical setting in an engaged and autonomous manner to allow for self-diagnosis, navigation, and advice.

Specifically, FIG. 4 conceptually illustrates a network architecture of a cloud-based autonomous mirroring diagnostic, navigation, and advice system 400 in some embodiments that hosts a cloud application service to which any personalized AI device connects to engage individuals to mirror personalized information normally accessible in a clinical setting in an engaged and autonomous manner to allow for self-diagnosis, navigation, and advice. The cloud-based autonomous mirroring diagnostic, navigation, and advice system 400 shown in this figure hosts a software application web service (or SaaS web application) for the MQ application running on any individually connected, personalized AI user device, such as mobile devices, tablet computing devices, smart mirrors, smart TVs, and/or other such personalized AI devices, to use in connection with engaging individuals to mirror personalized information, which would normally only be accessible in a clinical setting, and to do so in an engaged and autonomous manner, thereby providing an effect and private manner for users to interact or connect with others, self-diagnose various issues or feelings, navigate, and obtain advice.

As shown in this figure, the cloud-based autonomous mirroring diagnostic, navigation, and advice system 400 demonstrates a plurality of personalized AI devices 410-440 that connect over the cloud (Internet) to access an autonomous mirroring diagnostic, navigation, and advice cloud application service. To accomplish this, the cloud-based autonomous mirroring diagnostic, navigation, and advice system 400 includes several hardware and software-based service components. Specifically, the cloud-based autonomous mirroring diagnostic, navigation, and advice system 400 comprises the plurality of personalized AI devices 410-440, a wireless communication point 422 (e.g., a cell tower for cellular data communication), a gateway 424, a set of user authentication and registration server computing devices 450, a registered user database 460, a backend cloud server 470 with several backend server modules 472-478, a facial expression image database 480, and a mirror scripts and skills database 490. In some embodiments, the backend server modules 472-478 of the backend cloud server 470 includes a video conferencing and mirror conferencing connection module 472, a facial recognition processing module 474, a mirror deep learning and AI/ML system module 476, and a scripts and skills manager 478. In some embodiments, the plurality of personalized AI devices 410-440 includes a mirrored intelligence mobile client device 410 that is running the MQ application as configured to operate on mobile devices, a mirrored intelligence tablet device 420 running the MQ application as configured to run on tablet computing device, a smart mirror 430 running an embedded instance of the MQ application, and a smart TV 440 running another embedded instance of the MQ application.

In some embodiments, a plurality of external (or "third party") cloud services are accessible via the cloud-based autonomous mirroring diagnostic, navigation, and advice system 400. The plurality of external cloud services shown in this figure include third party AWS Amazon firestick & Alexa eco-system services 475, third party video streaming services 485, and an external AI/ML engine and deep learning services 495. However, the plurality of external cloud services may include more services than those shown in this figure, and are therefore understood to be exemplary and not limiting of the cloud-based autonomous mirroring diagnostic, navigation, and advice system 400. In some embodiments, the cloud-based autonomous mirroring diagnostic, navigation, and advice system 400 accesses the third party AWS Amazon firestick & Alexa eco-system services 475 for Amazon APIs and libraries associated with firestick and configured to allow users to create, build, and run Alexa skills and scripts. In some embodiments, the cloud-based autonomous mirroring diagnostic, navigation, and advice system 400 accesses the third party video streaming services 485 for video conferencing and mirror conferencing, as needed. In some embodiments, the cloud-based autonomous mirroring diagnostic, navigation, and advice system 400 accesses the external AI/ML engine and deep learning services 495 for training facial recognition, identification of users, and expressions, via images captured from the web cameras of the personalized AI devices of users.

The plurality of personalized AI devices 410-440 shown in this figure connect over the Internet (labeled "cloud") to the set of user authentication and registration server computing devices 450 to register or login as an existing registered user. Registered user information is stored in the registered user database 460. Unlike the mirrored intelligence tablet device 420 running the MQ application as configured to run on tablet computing device, the smart mirror 430 running an embedded instance of the MQ application, and the smart TV 440 running another embedded instance of the MQ application, which connect to the set of user authentication and registration server computing devices 450 directly over the Internet (or "cloud"), the mirrored intelligence mobile client device 410 connects to the set of user authentication and registration server computing devices 450 by way of a wireless connection to the wireless communication point 422 and through the gateway 424, finally connecting over the Internet (or "cloud") to the set of user authentication and registration server computing devices 450. While the example shown in this figure only illustrates the mirrored intelligence mobile client device 410 connecting via the wireless communication point 422 and through the gateway 424, a person of ordinary skill in the relevant art may understand that any of the personalized AI devices 410-440 configured to connect wirelessly by cellular or other wireless signal (e.g., the mirrored intelligence tablet device 420, the smart mirror 430, and/or the smart TV 440) are also able to connect via the wireless communication point 422 and through the gateway 424 (when so configured for the corresponding wireless communication).

Notably, a central aspect of the cloud-based autonomous mirroring diagnostic, navigation, and advice system 400 is the backend cloud server 470 with several backend server modules 472-478. In some embodiments, the backend cloud server 470 and the backend server modules 472-478 provides processing (at least in part) for the MQ-blended operating system 225 described above, by reference to FIGS. 2 and 3.

Furthermore, the backend cloud server 470 with the backend server modules 472-478 also performs runtime processing for video conferencing communication, connecting the video conferencing and mirror conferencing connection module 472 to the connecting personalized AI devices 410-440 and one or more video streaming services 485.

Additionally, the backend cloud server 470 with the backend server modules 472-478 also performs runtime processing for facial recognition via the facial recognition processing module 474, with video captured by the web camera 330 (described above, by reference to FIG. 3) being streamed to the backend cloud server 470 such that the facial recognition processing module 474 processes the video stream to identify faces of anyone in front of the smart mirror or other connecting device. In some embodiments, the facial recognition processing module 474 accesses the facial expression image database 480 to identify prior images of a particular user and compare a present image of the particular user with the prior images. In some embodiments, the facial recognition processing module 474 makes an external network connection to the external AI/ML engine and deep learning services 495 to perform the facial recognition processing, thereby being able to offload training and intense processing for facial recognition, identification of users, and expression recognition to an external service, so that the impact of processing is reduced.

In addition, the mirror deep learning and AI/ML system module 476 of some embodiments facilitates the connection between the facial recognition processing module 474 and the external AI/ML engine and deep learning services 495.

Moreover, the scripts and skills manager 478 of the backend cloud server 470 is configured to handle runtime processing of all skills and scripting via connection to the third party AWS Amazon firestick & Alexa eco-system services 475. The runtime processing of existing skills and scripts are initiated by a user through the MQ application via their individual personalized AI device. Once initiated, the backend cloud server 470 receives a skill name/identifier or a script name/identifier and retrieves the corresponding script or skill from the mirror scripts and skills database 490. In this way, any individual user may access saved/stored skills or scripts even when they obtain new personalized AI devices or switch between different personalized AI devices. Furthermore, by connecting to the cloud application service running on the backend cloud server 470, any of the individual users can create new skills and scripts through their personalized AI device, because a network connection would be established from the scripts and skills manager 478 of the backend cloud server 470 to the third party AWS Amazon firestick & Alexa eco-system services 475, thereby providing access to the relevant Amazon APIs and libraries associated with firestick.

In this way, the cloud-based autonomous mirroring diagnostic, navigation, and advice system 400, and the corresponding cloud application service to which the personalized AI devices 410-440 connect, can engage individual users to mirror their personalized information in ways that would normally only be possible in a clinical setting—but now can be performed anywhere to allow for self-diagnosis, navigation, advice, etc.

Many of the above-described features and applications are implemented as software programs or modules that carry out one or more processes. Some embodiments include electronic components, such as microprocessors, storage and memory that store computer program instructions in a machine-readable or computer-readable medium (alternatively referred to as computer-readable storage media, machine-readable media, machine-readable storage media, non-transitory computer readable medium, etc.). The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter. These software programs or modules which perform one or more of the processes described herein are each specified as a set of instructions recorded on a computer readable storage medium. When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

Also, in this specification, the terms "software", "application", and "program" and variations of these terms (collectively and individually referred to below as "software") are meant to include firmware residing in read-only memory or applications stored in magnetic storage, which can be read into memory for processing by a processor, such as the processor of a mobile computing device or a mobile communication device, such as a smartphone, a hand-held computing device, or a tablet computing device (referred to simply as a "mobile device"), a smart device, such as a smart mirror or a smart TV, or the processor of a traditional computing device, such as a server computer, a desktop computer, a single board computer ("SBC"), or a laptop computer (referred to simply as a "computer"). Also, in some embodiments, multiple software inventions can be implemented as sub-parts of a larger program while remaining distinct software inventions. In some embodiments, multiple software inventions can also be implemented as separate programs. In some embodiments, the software programs, when installed to operate on one or more electronic systems, define one or more specific machine implementations that execute and perform the operations of the software programs.

Figure 5:
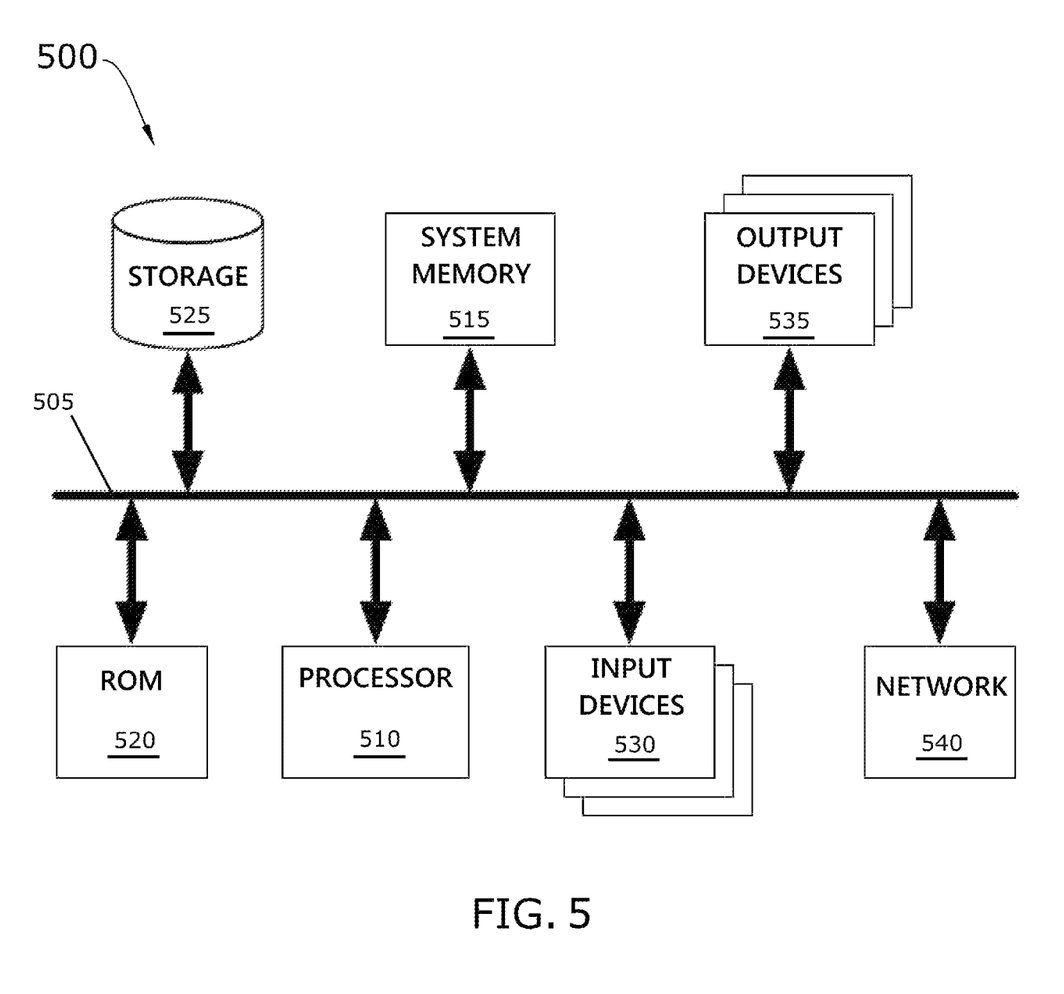

FIG. 5 conceptually illustrates an electronic system 500 with which some embodiments of the invention are implemented. The electronic system 500 may be a computer, mobile device, tablet, phone, PDA, or any other sort of electronic device. Such an electronic system includes various types of computer readable media and interfaces for various other types of computer readable media. Electronic system 500 includes a bus 505, processing unit(s) 510, a system memory 515, a read-only memory 520, a permanent storage device 525, input devices 530, output devices 535, and a network 540.

The bus 505 collectively represents all system, peripheral, and chipset buses that communicatively connect the numerous internal devices of the electronic system 500. For instance, the bus 505 communicatively connects the processing unit(s) 510 with the read-only memory 520, the system memory 515, and the permanent storage device 525.

From these various memory units, the processing unit(s) 510 retrieves instructions to execute and data to process in order to execute the processes of the invention. The processing unit(s) may be a single processor or a multi-core processor in different embodiments.

The read-only-memory (ROM) 520 stores static data and instructions that are needed by the processing unit(s) 510 and other modules of the electronic system. The permanent storage device 525, on the other hand, is a read-and-write memory device. This device is a non-volatile memory unit that stores instructions and data even when the electronic system 500 is off. Some embodiments of the invention use a mass-storage device (such as a magnetic or optical disk and its corresponding disk drive) as the permanent storage device 525.

Other embodiments use a removable storage device (such as a flash drive) as the permanent storage device 525. Like the permanent storage device 525, the system memory 515 is a read-and-write memory device. However, unlike storage device 525, the system memory 515 is a volatile read-and-write memory, such as a random access memory. The system memory 515 stores some of the instructions and data that the processor needs at runtime. In some embodiments, the invention's processes are stored in the system memory 515, the permanent storage device 525, and/or the read-only memory 520. For example, the various memory units include instructions for processing appearance alterations of displayable characters in accordance with some embodiments. From these various memory units, the processing unit(s) 510 retrieves instructions to execute and data to process in order to execute the processes of some embodiments.

The bus 505 also connects to the input and output devices 530 and 535. The input devices enable the user to communicate information and select commands to the electronic system. The input devices 530 include digital cameras (for facial recognition and occupancy detection, including either or both video and still image cameras, such as the web camera described above by reference to FIG. 3), microphones (for audio capture), remote controllers, and may also include alphanumeric keyboards and pointing devices (also called "cursor control devices"). The output devices 535 display images or videos in conference communication and output audio. The output devices 535 include speakers and display devices, such as liquid crystal displays (LCD) and organic light emitting diode (OLED) displays. Some embodiments include devices such as a touchscreen that functions as both input and output devices.

Finally, as shown in FIG. 5, bus 505 also couples electronic system 500 to a network 540 through a network adapter (not shown). In this manner, the computer can be a part of a network of computers (such as a local area network ("LAN"), a wide area network ("WAN"), or an intranet), or a network of networks (such as the Internet). Any or all components of electronic system 500 may be used in conjunction with the invention.

Also, the functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through networks.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

We claim:

1. An autonomous mirroring diagnostic, navigation, and advice system comprising:
    a personalized artificial intelligence (AI) interactive smart mirror device ("interactive smart mirror") operable by a particular user and configured to engage the particular user in mirroring personalized information through self-reflection, wherein the interactive smart mirror comprises a mirror surface, a housing, a single board computer (SBC) with a memory and a storage, a voice-assistance smart hub device, a camera, an occupancy sensor communicably connected to the camera, a mirrored intelligence (MQ) blended operating system that is loaded into the memory of the SBC during operation of the interactive smart mirror, a MQ application that is installed in the storage and runs on the SBC when loaded into the memory by the MQ blended operating system during operation of the interactive smart mirror, a nudging database that is communicably connected to the MQ blended operating system and stores a plurality of nudging elements, wherein the particular user specifies particular user preferences for a customized script by selection of particular nudging elements from the nudging database, wherein the customized script ensures individualized reflective interaction with the interactive smart mirror by the particular user;
    a plurality of personalized AI devices comprising the interactive smart mirror and at least one other personalized AI device;
    a backend cloud-based autonomous mirroring diagnostic, navigation, and advice server ("backend cloud server") comprising a video conferencing and mirror conferencing connection module ("video conferencing module"), a facial recognition processing module ("facial recognition module"), a mirror deep learning and artificial intelligence/machine learning (AI/ML) system module ("AI/ML module"), and a scripts and skills manager, wherein the backend cloud server hosts a cloud service to which the interactive smart mirror and the plurality personalized AI devices connect for processing of the video conferencing module, the facial recognition module, the AI/ML module, and the scripts and skills manager for the MQ blended operating system to engage the particular user of the interactive smart mirror and users of the plurality personalized AI devices to mirror personalized information for self-diagnosis, navigation, and advice, wherein the video conferencing module triggers the camera of the interactive smart mirror to capture video and stream the captured video over a video stream connection to the backend cloud server when the occupancy sensor of the interactive smart mirror detects a user reflected in the mirror surface of the interactive smart mirror;
    a facial expression image database communicably connected to the facial recognition module of the backend cloud server, wherein the facial recognition module is configured to (i) access the facial expression image database to identify prior images of the particular user stored in the facial expression image database and (ii) compare a present image of the particular user, captured by the camera of the interactive smart mirror and received by the video conferencing module of the backend cloud server, with the prior images of the particular user stored in the facial expression image database; and a mirror scripts and skills database communicably connected to the scripts and skills manager of the backend cloud server, wherein the customized script is stored in the mirror scripts and skills database and is retrieved by the scripts and skills manager for processing of skills and scripting associated with the customized script when the user reflected in the mirror surface as detected by the occupancy sensor is determined to be the particular user based on the comparison, by the facial recognition module, of the present image and prior images of the particular user.

2. The autonomous mirroring diagnostic, navigation, and advice system of claim 1, wherein the mirror scripts and skills database stores a set of mirror skills and a set of mirror scripts, wherein the mirror skills and the mirror scripts are accessible to the scripts and skills manager of the backend cloud server.

3. The autonomous mirroring diagnostic, navigation, and advice system of claim 1, wherein the AI/ML module comprises a mirror deep learning module and a mirror artificial intelligence/machine learning (mirror AI/ML) module that is separate from the mirror deep learning module.

4. The autonomous mirroring diagnostic, navigation, and advice system of claim 2, wherein the mirror scripts and skills database further stores a set of magic mirror scripts, wherein the mirror scripts stored in the mirror scripts and skills database are PHP scripts, wherein the magic mirror scripts are different from the PHP mirror scripts stored in the mirror scripts and skills database.

5. The autonomous mirroring diagnostic, navigation, and advice system of claim 1, wherein the camera of the interactive smart mirror comprises a web camera.

6. The autonomous mirroring diagnostic, navigation, and advice system of claim 5, wherein the voice-assistance smart hub device comprising a microphone and an audio speaker.

\* \* \* \* \*